US006327033B1

(12) United States Patent
Ferguson et al.

(10) Patent No.: US 6,327,033 B1
(45) Date of Patent: Dec. 4, 2001

(54) DETECTION OF PHASE DEFECTS ON PHOTOMASKS BY DIFFERENTIAL IMAGING

(75) Inventors: Richard A. Ferguson, Pleasant Valley; Alfred K. Wong, Beacon, both of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/336,445

(22) Filed: Jun. 21, 1999

(51) Int. Cl.$^7$ ................................................. G01B 11/00
(52) U.S. Cl. .............................................................. 356/394
(58) Field of Search ..................................... 356/394, 398, 356/237.1, 392, 430, 431, 237.2–237.5, 239.1, 239.7, 239.8; 250/562, 572; 358/101, 106, 107

(56) References Cited

U.S. PATENT DOCUMENTS

| 5,270,796 | 12/1993 | Tokui et al. | 356/394 |
| 5,353,116 | 10/1994 | Tanigawa et al. | 356/390 |
| 5,786,112 | 7/1998 | Okamoto et al. | 430/5 |

OTHER PUBLICATIONS

Watanabe, et al., "Detection and Printability of Shifter Defects in Phase–Shifting Masks II. Defocus Characteristics" Jpn. J. Appl. Phys. vol. 31 (1992) pp. 4155–4160 Part 1, No. 12B Dec. 1992.

T. Chieu, et al. "Fabrication of Phase Shifting Masks Employing Multi Layer Films," Proc. SPIE, vol. 2197, pp. 181–193, 1994.

D. Emery, et al., "Detection of 60° Phase defects on Alternating PSMs", SPIE vol. 3412 pp. 480–485, Apr. 1998.

Primary Examiner—Frank G. Font
Assistant Examiner—Michael P. Stafira
(74) Attorney, Agent, or Firm—H. Daniel Schnurmann

(57) ABSTRACT

A method for detecting phase features or phase defects on photomasks for optical lithography is described. The asymmetric imaging behavior through focus of defects or features with a phase other than 0° or 180° is used to distinguish them from other features on the mask. The mask is inspected at equally spaced positions about an optimum focus in both positive and negative directions. The images are subtracted from one another to produce a differential image of the mask. While opaque features as well as transmitting features at 0° and 180° behave identically at positive and negative defocus, thus leading to a zero-valued differential image, the focus asymmetry of phase defects and features produces a non-zero differential image from which these phase defects and features can be located. By comparing the locations on the mask for which a non-zero differential image is obtained with the designed data for the mask, the phase defects can be sorted from the phase features and the absence of phase features can be detected. Additional image processing can be applied to verify the integrity of the phase features. The differential image inspection technique can be implemented on existing optical inspection tools by employing a two-pass inspection performed at positive and negative defocus in sequence. In addition, a new apparatus with parallel inspection optics is described for inspecting the mask at positive and negative focus simultaneously.

24 Claims, 12 Drawing Sheets

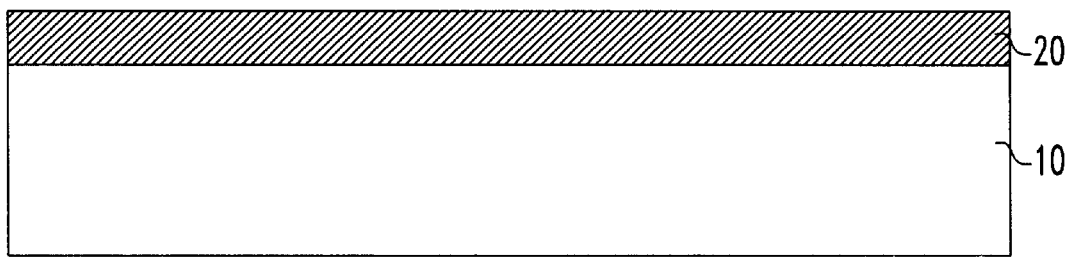
FIG. 1a    (PRIOR ART)
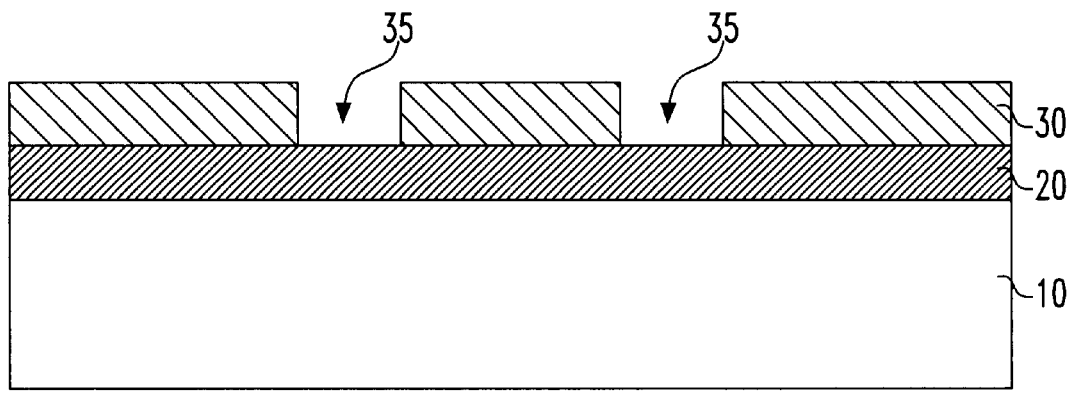
FIG. 1b    (PRIOR ART)
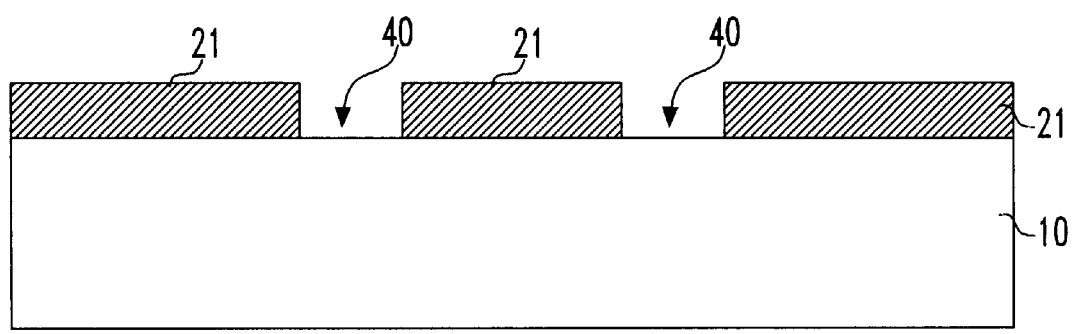
FIG. 1c    (PRIOR ART)

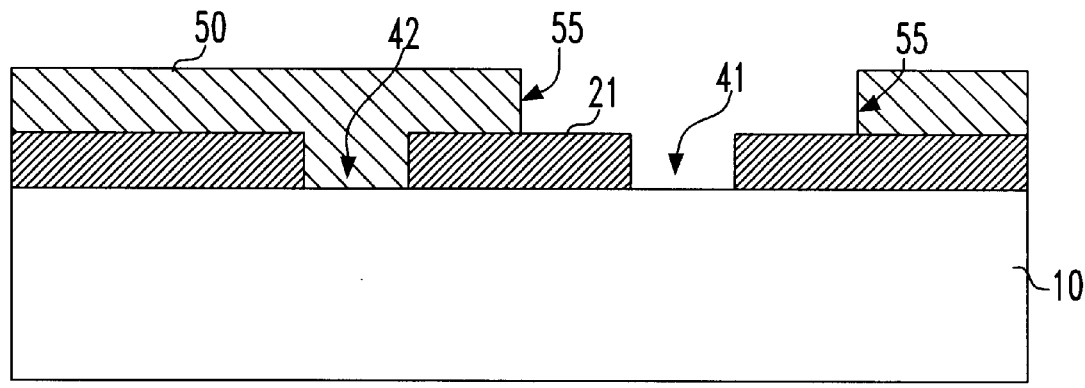
*FIG. 2a     (PRIOR ART)*
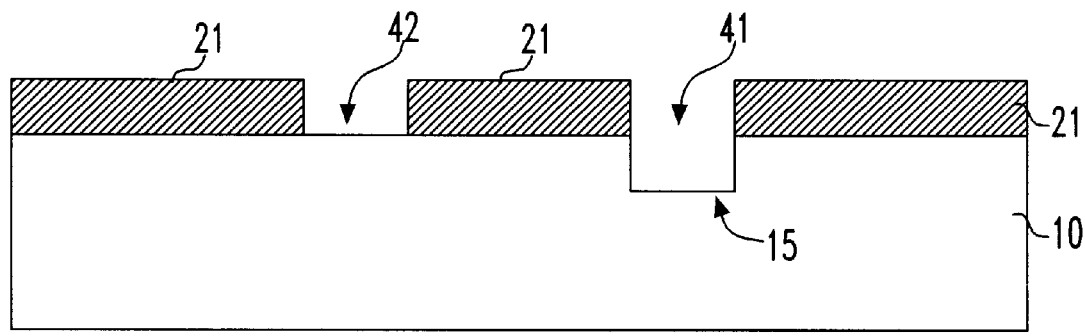
*FIG. 2b     (PRIOR ART)*

DETECTION OF PHASE DEFECTS ON PHOTOMASKS BY DIFFERENTIAL IMAGING

FIELD OF THE INVENTION

This invention relates, generally, to photolithography, and more particularly, to a method and apparatus for detecting phase defects and other phase features on a photomask using differential imaging.

BACKGROUND OF THE INVENTION

In the photolithography step of integrated circuit manufacturing, a template containing a designed set of clear and dark shapes, referred to as the mask or reticle, is repeatedly printed on the surface of a silicon wafer. This process is achieved by way of optical imaging at an image size resolution defined primarily by the wavelength ($\lambda$), numerical aperture (NA) and partial coherence ($\sigma$) of the optical projection system (hereinafter referred to as the stepper).

In standard industry practice as outlined in the schematic mask cross-section of FIG. 1, the masks containing the desired opaque and clear patterns are fabricated starting from an initial mask blank (FIG. 1a) consisting of a substrate which is transparent to the imaging light (10), coated on one side with an opaque film (20). Typically, the transparent substrate consists of fused silica (also known as quartz) and which will, hereinafter, be referred to as the quartz substrate whereas the transparent substrate material will be referred to as quartz. Moreover, the opaque film is typically a chromium-based material, referred to hereinafter as the chrome film, while the material of the film itself being referred to as chrome. The designed shapes are replicated on this mask blank by first selectively patterning (or "writing") the designed shapes in a protective material which is characterized as being sensitive to electron or optical exposure (FIG. 1b), hence forth referred to as the resist (30). The openings created in the resist via selective patterning (35) are then transferred to the underlying chrome film during a subsequent etch step such that, following removal of the resist material (FIG. 1c), the designed clear shapes (40) and opaque shapes (21) are replicated in the final patterned mask. Masks fabricated in this manner will be referred to, hereinafter, as standard or chrome-on-glass (COG) masks.

A different class of masks, phase-shifting masks (PSM), have demonstrated the capability of extending resolution beyond conventional imaging limits by taking advantage of both the phase and the magnitude of the imaging light. If two clear shapes which transmit light of opposite phases (180° phase difference) are placed in close proximity to one another, the phase difference will produce a destructive interference null between the two shapes. Such a mask has been given several different designations in the literature such as Levenson, Levenson-Shibuya, phase edge, alternating aperture, or alternating mask. Herein, it will be referred to as an alternating mask or an alternating PSM. The additional mask fabrication steps beyond the standard mask process of FIG. 1 are shown for an etched-quartz or subtractive alternating PSM process in FIG. 2.

With reference to FIG. 2, a phase difference between two clear shapes for the alternating PSM is achieved in standard industry practice by selectively etching into the quartz substrate (10), such that an optical path difference equivalent to the desired phase offset is obtained between the two adjacent openings. Following standard mask patterning as shown in FIG. 1, a second write step is used to selectively open a protective resist coating (50) for the phase-shifted opening (41) leaving the non-phase shifted opening (42) covered, as shown in FIG. 2a. In practice, it is desirable to locate the edges of the resist pattern (55) some distance away from the phase-shifted opening (41) and on top of the opaque chrome shapes (21) where appropriate, in order to use the chrome itself as an etch barrier and to account for overlay (or pattern placement) errors between the first and second-level write steps in the fabrication process. The quartz is then etched (typically with an anisotropic reactive-ion etch (RIE) process) to a depth of approximately:

$$\text{etch depth} = \text{phase} * \lambda / [2 * \pi * (n-1)] \quad (1)$$

wherein n is the refractive index of the quartz substrate at wavelength $\lambda$ and the phase of the opening (41) is given in radians. Following removal of the resist (50), the resultant alternating PSM has the etched-quartz trench (15) providing the desired phase difference between adjacent openings (41) and (42), as shown in FIG. 2b.

Other fabrication methods have been proposed. One of such approaches provides an accurate control of the phase, as determined by equation (1), through the addition of multi-layer films to the transparent substrate. More details may be obtained from an article by Chieu et al. entitled Fabrication of Phase Shifting Masks Employing Multi Layer Films, published in the Proc. SPIE, Vol. 2197, pp. 181–193, 1994, wherein a mask blank is described having two additional layers added between the transparent quartz substrate and the opaque chrome: an etch stop layer composed of either $Al_2O_3$ or $HfO_2$ and a transparent layer of silicon dioxide at a controlled thickness given by equation (1). By etching into the silicon dioxide until the etch stop layer is reached, the desired phase is then achieved. Alternatively, additive fabrication methods can be used to achieve the desired phase shift such as through the application and selective patterning of a transparent spin-on-glass following the standard mask fabrication procedures illustrated in FIG. 1. Regardless of the fabrication specifics, all of these techniques are generally categorized as an alternating PSM.

Defect-free masks are required for integrated circuit manufacturing (i.e., the patterns on the mask need to accurately replicate the designed data). In order to ensure defect-free masks following fabrication, the mask manufacturer will perform an automated optical inspection of the completed reticle to search for unwanted defects on the mask by comparing images of the mask from the optical inspection system to either the design database (hereinafter referred to as die-to-database inspection) or to the image from an exactly replicated pattern elsewhere on the mask (hereinafter referred to as die-to-die inspection). This inspection is typically performed on high-NA optical systems at wavelengths within the UV spectrum. For example, a state-of-the-art inspection system from KLA uses a 364 nm wavelength with a numerical aperture of 0.625. The defect inspection step can be further classified as either actinic (i.e., the inspection wavelength is the same as the exposure wavelength of the intended stepper) or non-actinic (i.e., the inspection wavelength is not the same as the exposure wavelength of the intended stepper).

An inspection system as described is used in standard practice for detecting defects such as shown in FIG. 3a in cross-sectional view and FIG. 3b in top-down view for the desired design shown in FIG. 3c. Opaque shapes (110) and (120) are contained on the representative mask schematics of FIG. 3a and FIG. 3b, but an extra opaque shape (130) not contained in the design data of FIG. 3c has been inadvertently added to the designed shapes as shown in FIGS. 3a and 3b. This defect is expected to cause an anomalous printing effect during lithographic patterning of the defective mask (i.e., defect 130) printing and/or causing variation in the shape or size of desired features (110) and (120) on the wafer) when the size of this opaque shape is on the order of one-third the minimum feature size or larger. Such defects may result from, but are not limited to, partial blockage of the chrome etch between the fabrication steps shown in FIGS. 1b–1c, or mask contamination by opaque, foreign material (FM) prior to mask inspection.

Generally, state-of-the-art inspection systems have demonstrated the capability to successfully find such printable defects. State-of-the-art inspection systems, however, are less adept at detecting transparent phase defects with small phase (relative to 0° or 180°) and/or size, and yet such defects can also have an anomalous effect on the printed image on the wafer. FIG. 4 indicates a possible phase defect on a standard COG mask comprising the small region of the quartz substrate (230) in between desired chrome shapes (210) and (220) which has been accidentally etched during fabrication or repair. The size of the transparent phase defect is determined by the lateral dimension of the defect while the phase of the defect is determined by the average depth of the defect relative to the surrounding quartz as given by equation (1). FIG. 5 provides an example of a phase defect in an alternating PSM wherein the defect consists of unetched quartz (330) within the 180° designed feature (340) between opaque features (310) and (320). Watanabe et al., in the article "Detection and printability of shifter defects in phase shifting masks II., Defocus characteristics", published in the Japan Journal of Applied Physics, Vol. 31 (1992), pp. 4155–4160, Part 1, No. 12B, have demonstrated that phase defects may be more likely to print under conditions where the stepper is not operating at a focal position for which the image contrast of the desired features is maximized (i.e., the stepper is defocused from its 'best' or optimum focus).

The difficulty of detecting small phase defects is demonstrated by a simulated inspection image, as shown in FIG. 6, obtained from an actinic inspection of a 20° phase defect, as illustrated in FIGS. 5a and 5b, with the image shown being representative of standard industry practice today (i.e., at optimum focus with state-of-the-art optical parameters). The chrome lines (310) and (320) image at low intensity, the 180° phase region images at bright intensity, while the 20° phase defect (330) causes only a small anomaly as indicated.

State of the art inspection systems also have difficulty in detecting the presence and/or the integrity of phase features on the mask. FIG. 7a provides an example of a phase-shifted design in which shape (510) is assigned a 0° phase, while shape (520) is assigned a phase of 180°. FIG. 7b demonstrates a possible "missing shifter" configuration based on FIG. 7a, wherein pattern (530) is processed properly to match desired shape (510), even though feature (540) was not fabricated to the proper phase of 180° (i.e., the phase-shift processing steps of FIGS. 2a–2b were not successfully achieved). The inspection images using standard industry practice for the properly fabricated shapes and for the missing shifter pattern are given in FIGS. 8a–8b, respectively. The small difference between the two images indicates that inspection methods practiced today are not sufficient for detecting the absence of the phase shifted pattern on shape (540).

Other techniques have been proposed to improve inspection capabilities that enable to detect the presence of phase defects. By way of example:

In U.S. Pat. No. 5,270,796 to Tokui et al., an inspection tool is described wherein a phase contrast microscope is used to generate a phase signal which is compared with a reference signal in order to detect phase defects.

Spence et al. in an article entitled "Detection of 60° phase defects on alternating PSMs", SPIE vol. 3412, pp. 480–495, describe a method by which both the reflected and transmitted light from adjacent die are used in order to detect 60° phase defects on alternating phase shift masks.

OBJECTS OF THE INVENTION

Accordingly, it is an object of the invention to provide a method for detecting defects and other phase features on a photomask using differential imaging.

It is another object of the invention to employ a two-pass inspection scheme to obtain the differential images by measuring photomask images at a positive and at a negative focus sequentially.

It is still another object of the invention to provide an inspection apparatus which generates the differential image in a single pass, by inspecting the mask simultaneously at both a positive and a negative focus (with respect to the optimum focus) using parallel optical systems.

SUMMARY OF THE INVENTION

The present invention is intended to provide a method for detecting phase features or phase defects on photomasks for optical lithography. More specifically, the asymmetric imaging behavior through focus of defects or features with a phase other than 0° or 180° is used to distinguish them from other features on the mask. The mask is inspected at equally spaced positions about an optimum focus in both positive and negative direction. The images are subtracted from one another to produce a differential image of the mask. While opaque features as well as transmitting features at 0° and 180° behave identically at positive and negative defocus, thus leading to a zero-valued differential image, the focus asymmetry of phase defects and features produces a non-zero differential image from which these phase defects and features can be located.

In a first aspect of the invention, there is provided a method for detecting phase features or phase defects on a photomask which includes the steps of: collecting images at the photomask at multiple focal planes of an optical inspection tool, the focal planes being positioned in a positive and a negative direction about an optimum focus of the optical inspection tool; and identifying elements of the images which behave asymmetrically relative to the optimum focus, the elements being categorized as the phase features or phase defects.

In a second aspect of the invention, there is provided a method for detecting phase features or phase defects on a photomask which includes the steps of: collecting images of the photomask at multiple focal planes of an optical inspection tool, the focal planes being positioned in a positive and a negative direction about an optimum focus of the optical inspection tool; calculating a differential image of the mask by subtracting a first one of the images collected in one direction from a second one of the images collected at an opposite direction about the optimum focus; and identifying elements of the images having an absolute value larger than a fixed threshold which result in a non-zero value for the differential image, the non-zero value defining the phase features or phase defects.

In a third aspect of the invention, there is provided an apparatus for detecting phase features or phase defects on a photomask which includes: means for collecting images at multiple focal planes of an optical inspection tool, the focal planes being positioned in a positive and a negative direction about an optimum focus provided by the optical inspection tool; means for calculating a differential image of the mask by subtracting a first one of the images collected in one direction from a second one of the images collected at an opposite direction about the optimum focus; means for identifying elements of the images which result in a non-zero value for the differential image, the non-zero value defining the phase features or phase defects; and means for comparing the location of the element at which the differential image exceeds a threshold of a predetermined data set representing desired phase features on the photomask, wherein an unmatched one of the locations is categorized as a phase defect.

BRIEF DESCRIPTION OF THE DRAWINGS

While the specification concludes with claims particularly pointing out and distinctly claiming what is regarded as the present invention, details of a preferred embodiment of the invention may be more readily ascertained from the technical description when read in conjunction with the accompanying drawings, wherein:

FIGS. 1a–1c show a sequence of prior art mask fabrication steps for a standard COG mask in cross-section;

FIGS. 2a–2b show an additional sequence of prior art mask fabrication steps for an etched-quartz alternating PSM in cross section;

FIGS. 3a–3c show a typical opaque defect present in a standard COG mask, wherein FIGS. 3a–3b illustrate, respectively, a cross-section and a top-down view of defects applicable to the design data shown in FIG. 3c;

FIGS. 4a–4c show a typical phase defect present in a standard COG mask, wherein FIGS. 4a–4b illustrate, respectively, a cross-section and a top-down view of defects applicable to the design data shown in FIG. 4c;

FIGS. 7a–7b illustrate an example of a missing shifter in an alternating PSM, wherein FIG. 7a shows the desired pattern in which a first shape is assigned a 0° phase and a second shape is assigned a phase of 180°, and wherein FIG. 7b shows a possible error in which the 180° is improperly fabricated at 0°.

PREFERRED EMBODIMENT OF THE INVENTION

Figure 3A:
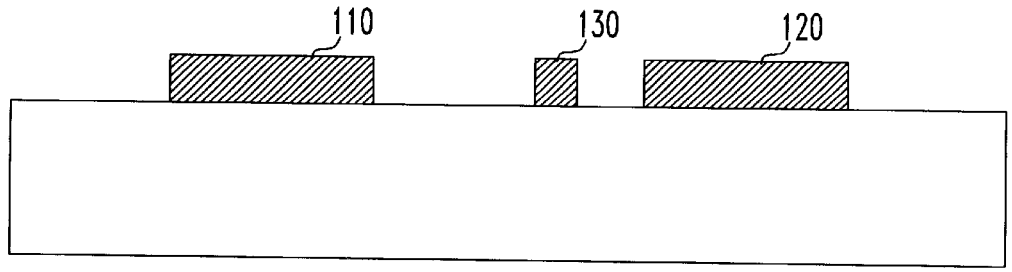
Figure 3B:
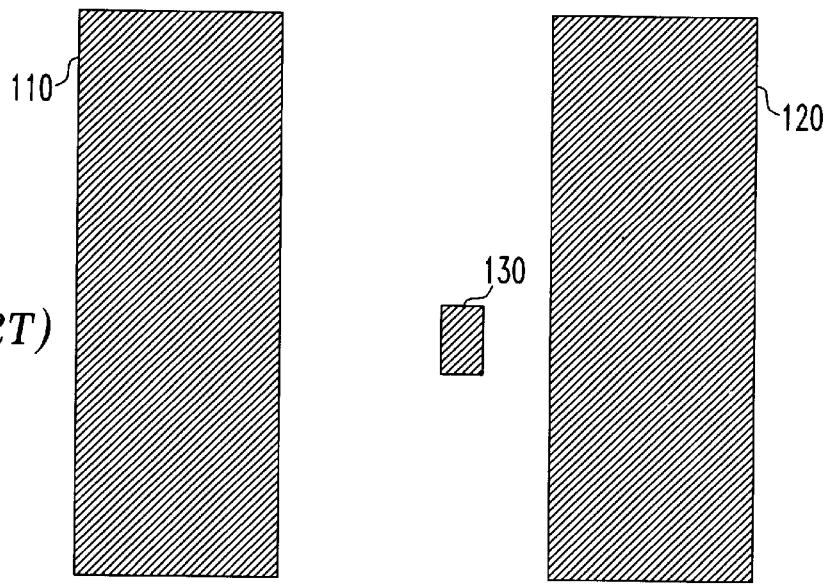
Figure 3C:
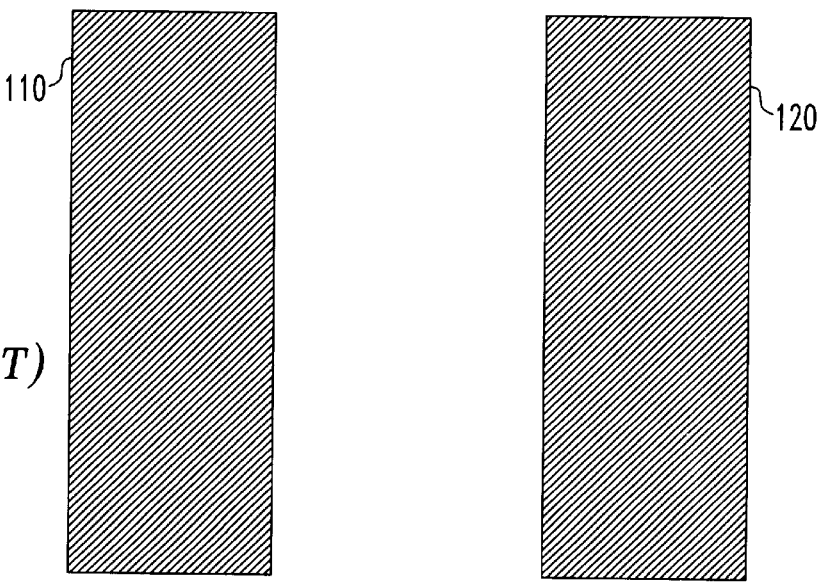
Figure 4A:
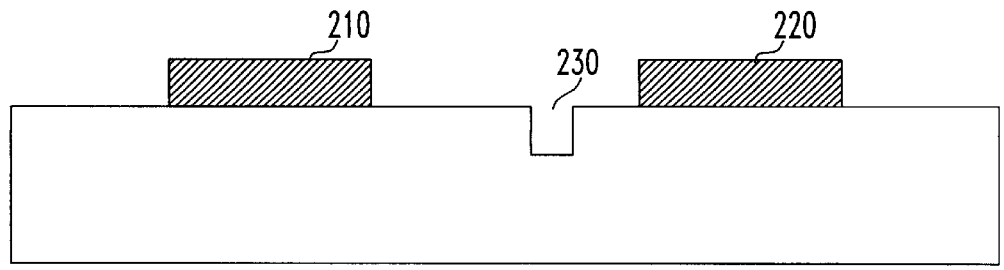
Figure 4B:
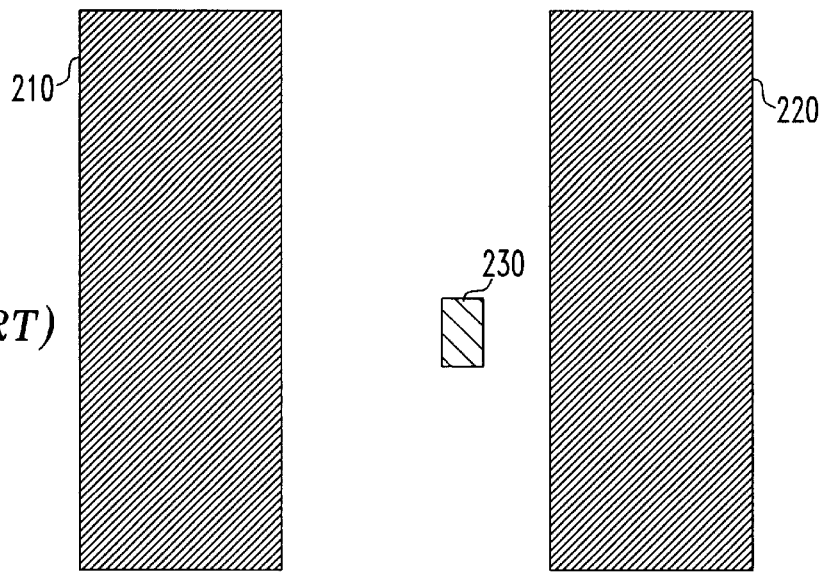
Figure 4C:
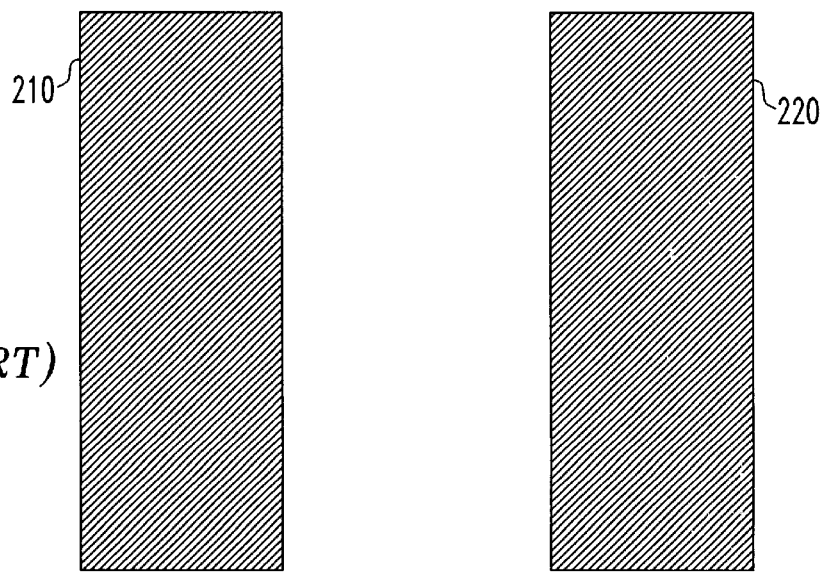
Figure 5A:
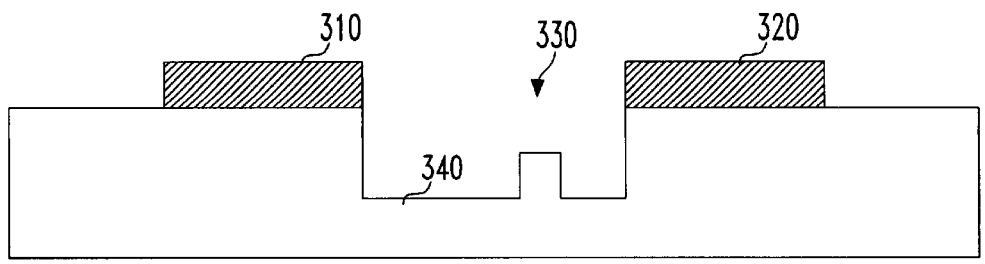
FIGS. 5a–5c illustrate an example of a conventional phase defect in an alternating PSM, wherein the defect consists of unetched quartz within the 180° designed feature between two opaque features.
Figure 5B:
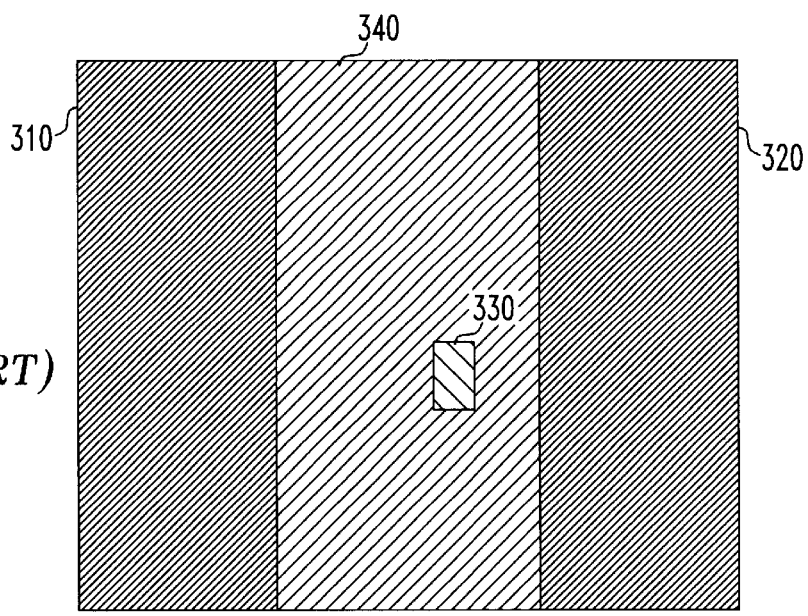
Figure 5C:
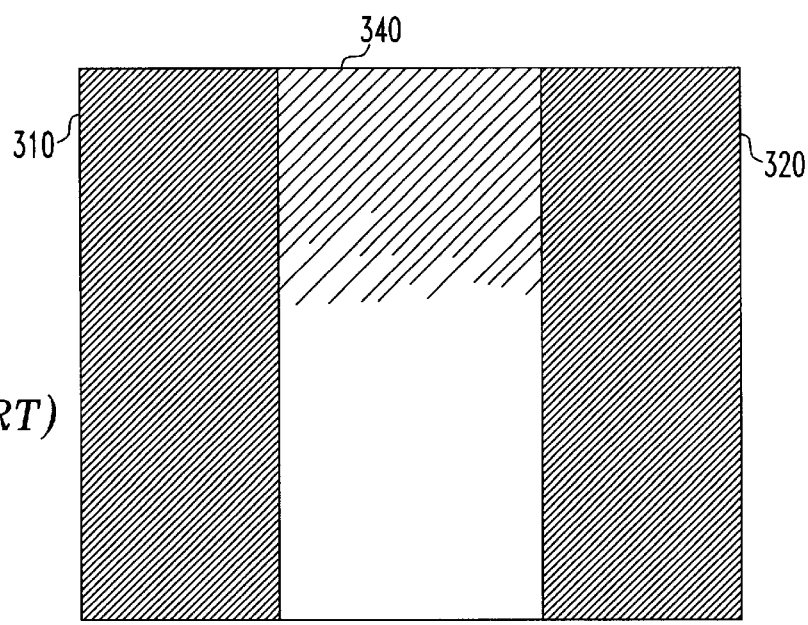

The invention described herein for detecting phase defects on a mask takes advantage of asymmetric imaging characteristics that occur as a function of focal position when the phase of a feature (defined hereinafter as a desired shape on the mask) or defect (defined hereinafter as an undesired shape on the mask) does not equal to 0° or 180° or some multiple thereof as defined in equation (1), wherein $\lambda$ is the optical inspection wavelength. In the preferred embodiment of this invention a fabricated mask (either COG or PSM as described in the background section) which may contain phase defects or features is illuminated by light at the inspection wavelength and the transmitted (or reflected) image of the mask is measured by an optical lens or objective at two focus positions that are equally spaced about the optimum focus, also referred to as "best" focus (i.e., at a focal position which produces the maximum image contrast of the mask patterns) in a positive and negative direction (i.e., arbitrarily defined herein as moving the mask towards and away from the imaging lens, respectively). Typically, the area to be inspected on the mask is much larger than the field size of the imaging lens such that the mask must be scanned relative to the field location of the imaging optics (e.g., the mask is secured to a high-precision scanning stage during inspection) The images of the mask at positive and negative focus may be collected concurrently or sequentially in any order. The magnitude of the defocus (i.e., the distance from optimum focus) is selected such that reasonable image integrity is maintained for mask patterns that are desired to be resolved during the photolithographic patterning step such as a defocus step size of ±1 Rayleigh unit as defined by:

$$\text{Rayleigh unit} = \lambda_i / (2 * NA_i * NA_i) \qquad (2)$$

where $\lambda_i$ is the inspection wavelength and $NA_i$ is the numerical aperture of the inspection objective. The magnitude of the defocus can be adjusted or optimized in order to tune the sensitivity of the inspection to highlight certain phase defects or feature at a size and/or phase of interest, as illustrated by the focus sensitivity to phase error of FIG. 6 in the aforementioned article by Watanabe.

Upon inspection in this dual focus mode, all objects on the mask that are opaque or which have a phase of 0° or 180° will produce identical images at each of the two focus positions spaced symmetrically about an optimum focus. Features and defects with a phase other than 0° or 180°, however, will not image identically at positive and negative focus, such as was described in the aforementioned article by Watanabe et al. Thus, in the preferred embodiment of this invention, the inspection images collected at the two defocus conditions, as described in the preceding paragraph, are subtracted from one another at each location on the mask to obtain a differential image of the mask. In this differential image, the asymmetric focus behavior of phase defects or features produces a non-zero differential image while for all other features the differential image will cancel (i.e., result in a zero background intensity). Calculation of the differential image may performed during inspection as the defocused images of the mask are measured, if positive and negative focus are measured simultaneously, or the images obtained at the two focus conditions may be stored for calculation of the differential image after the entire mask has been inspected. Once the differential image has been calculated, the phase defects are located by searching for non-zero values in the differential image. In actuality, noise within the image measurements will likely require that some minimum threshold value of the differential image be established to indicate the presence of a phase defect or feature. For locations at which the threshold has been exceeded, comparison of the differential image with the designed data can be used to differentiate between a phase defect and a desired phase feature contained within the design data. Detection of defects adjacent to or contained within phase features may require more sophisticated image processing algorithms similar to proprietary algorithms used on existing inspection tools today for detecting non-phase defects adjacent to non-phase features. A die-to-die inspection methodology can also be employed, wherein the differential image is compared between two areas on the mask for which the designed data is identical; any mismatches in the differential image are then identified as defects. An in-focus inspection as commonly practiced today can be combined with the embodiment of this invention as described in order to detect the non-phase defects as well.

Figure 6:
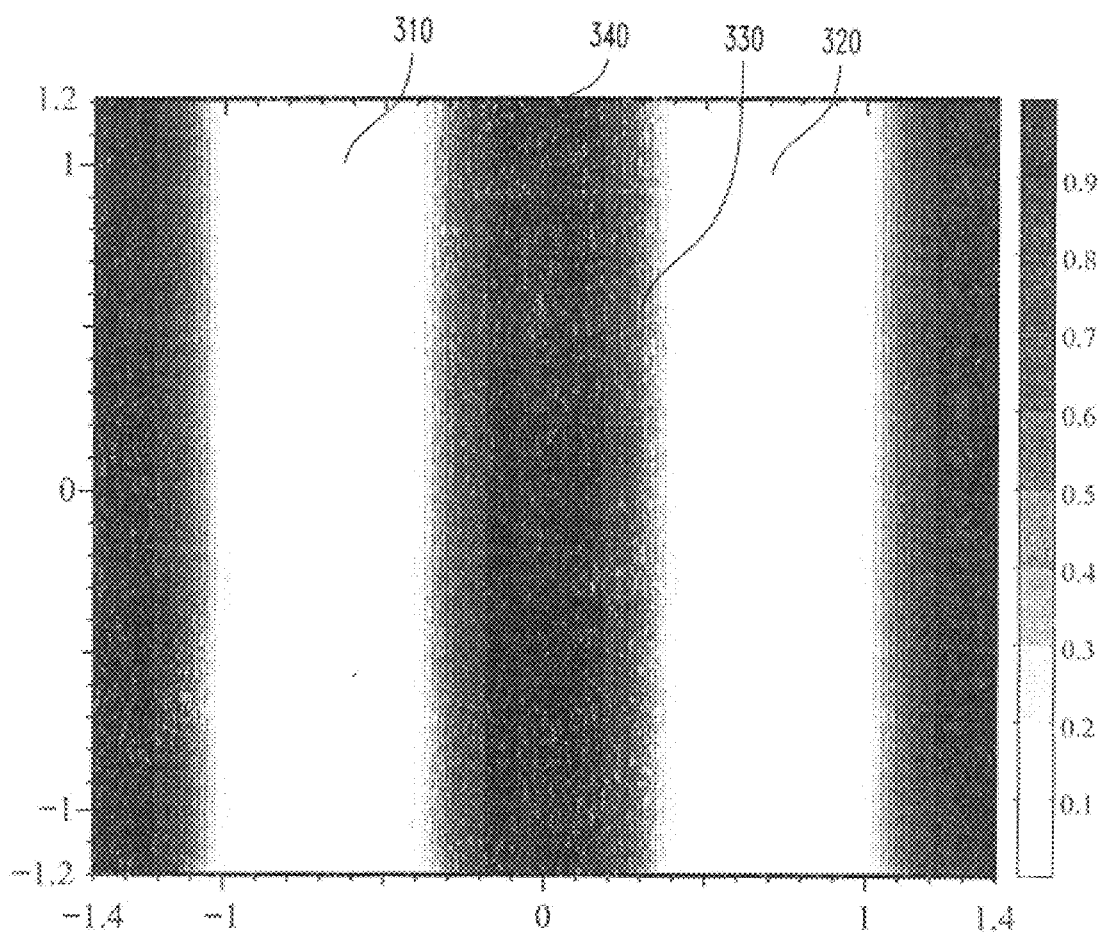
FIG. 6 shows the results of simulating the inspection image obtained from a prior art inspection system for a 20° phase defect in an alternating PSM pattern, such as illustrated in FIG. 5.
Figure 9:
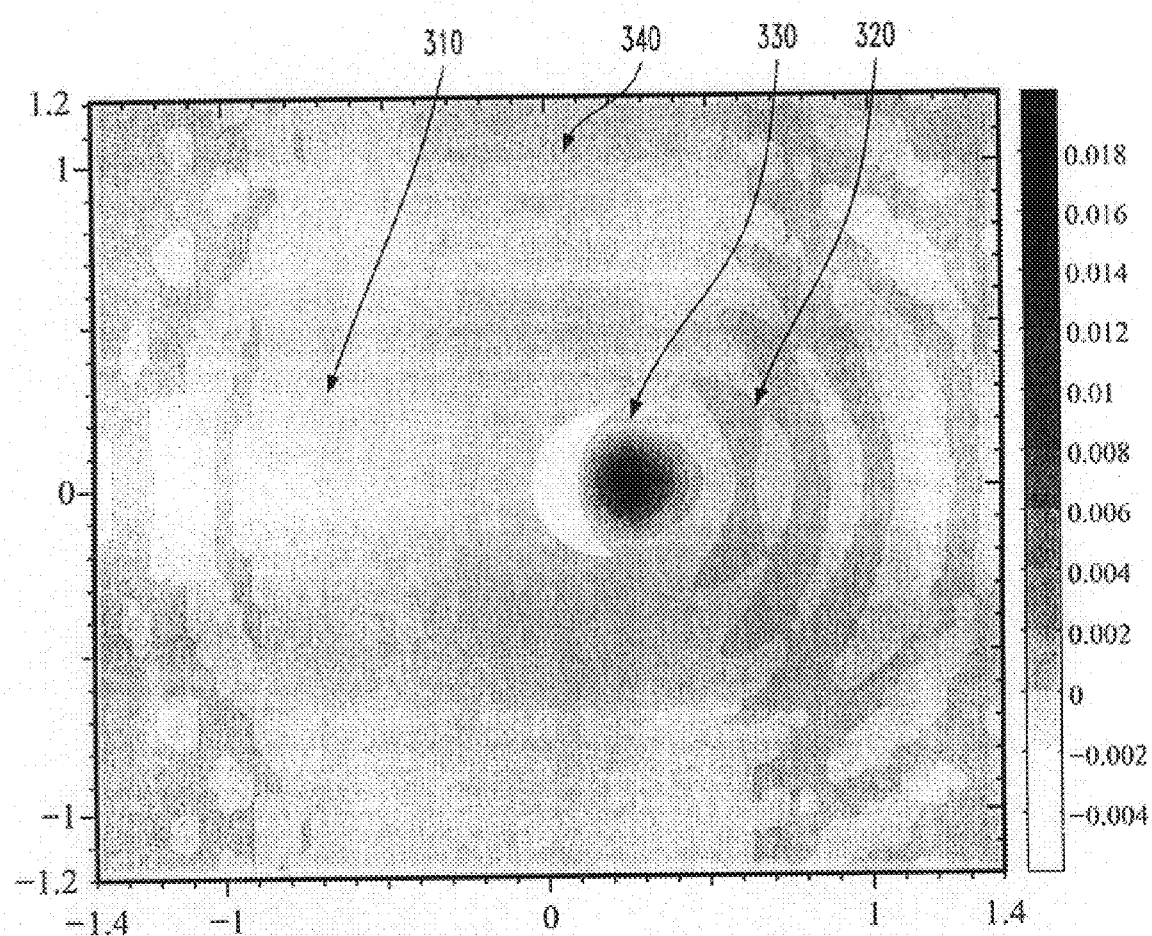
FIG. 9 represents the results of simulating the differential image obtained from dual focus images at ±1 Rayleigh unit of defocus, in accordance with the present invention, for a 20° phase defect in an alternating PSM, such as shown in FIG. 5.

The simulation of the resultant differential image representing the preferred embodiment of this invention is shown in FIG. 9, as obtained from the dual focus images taken at ±1 Rayleigh unit of defocus for the same alternating PSM as illustrated in FIG. 6, for a prior art inspection. The impact of the phase defect (330) becomes clearly highlighted in the differential image while the features that image symmetrically through focus (310, 320, 340) recede to a background differential intensity near zero. The sensitivity of the differential image to the phase defect shown in FIG. 9 compares favorably to the lack of sensitivity demonstrated by prior art inspection, as illustrated in FIG. 6.

Figure 10:
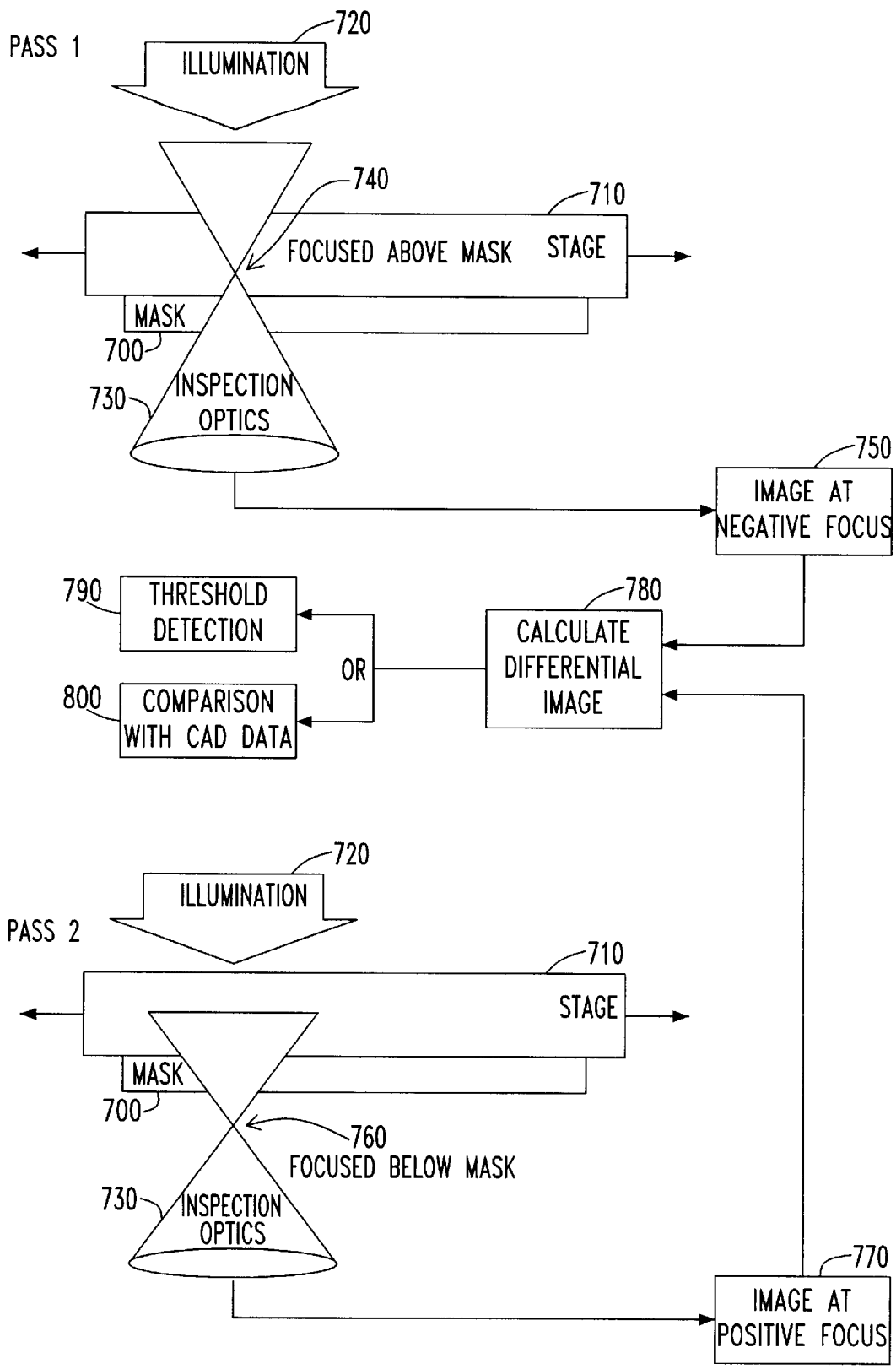
FIG. 10 shows a schematic diagram demonstrating the application of a prior art apparatus in which a two-pass inspection apparatus is used to obtain a differential image.

A schematic diagram that demonstrates a method by which this invention can be implemented on an existing apparatus comparable to state-of-the-art systems is illustrated in FIG. 10. The method employs an optical inspection tool comprising illumination light (720), stage (710), and inspection optics (730) in a two pass inspection to obtain the differential image, as described previously. The mask to be inspected for phase defects (700) is secured to the moveable stage of the inspection system (710). The mask is illuminated by the inspection wavelength (720) and the transmitted image across the mask is captured by the inspection optics (730) as the stage is scanned. In the first-pass inspection of the mask, the inspection optics are purposefully focused above the mask shapes (740) and the defocused image stored (750) (previously defined herein as the negative focus direction). A similar procedure is followed in a second-pass inspection of the entire mask in which the inspection optics is purposefully focused in the positive direction below the mask shapes (760) with this image at positive focus likewise also stored (770). The dual focus images are then spatially aligned and subtracted from one another at each location on the mask to obtain the differential image (780). With the differential image thus captured, a simple threshold detection algorithm (790) can be used to find any defects that result in a non-zero differential image.

For non-actinic inspection, more sophisticated algorithms may be required to filter out the effects on the differential image of designed phase shapes the locations of which are obtained from the CAD data (800).

Figure 11:
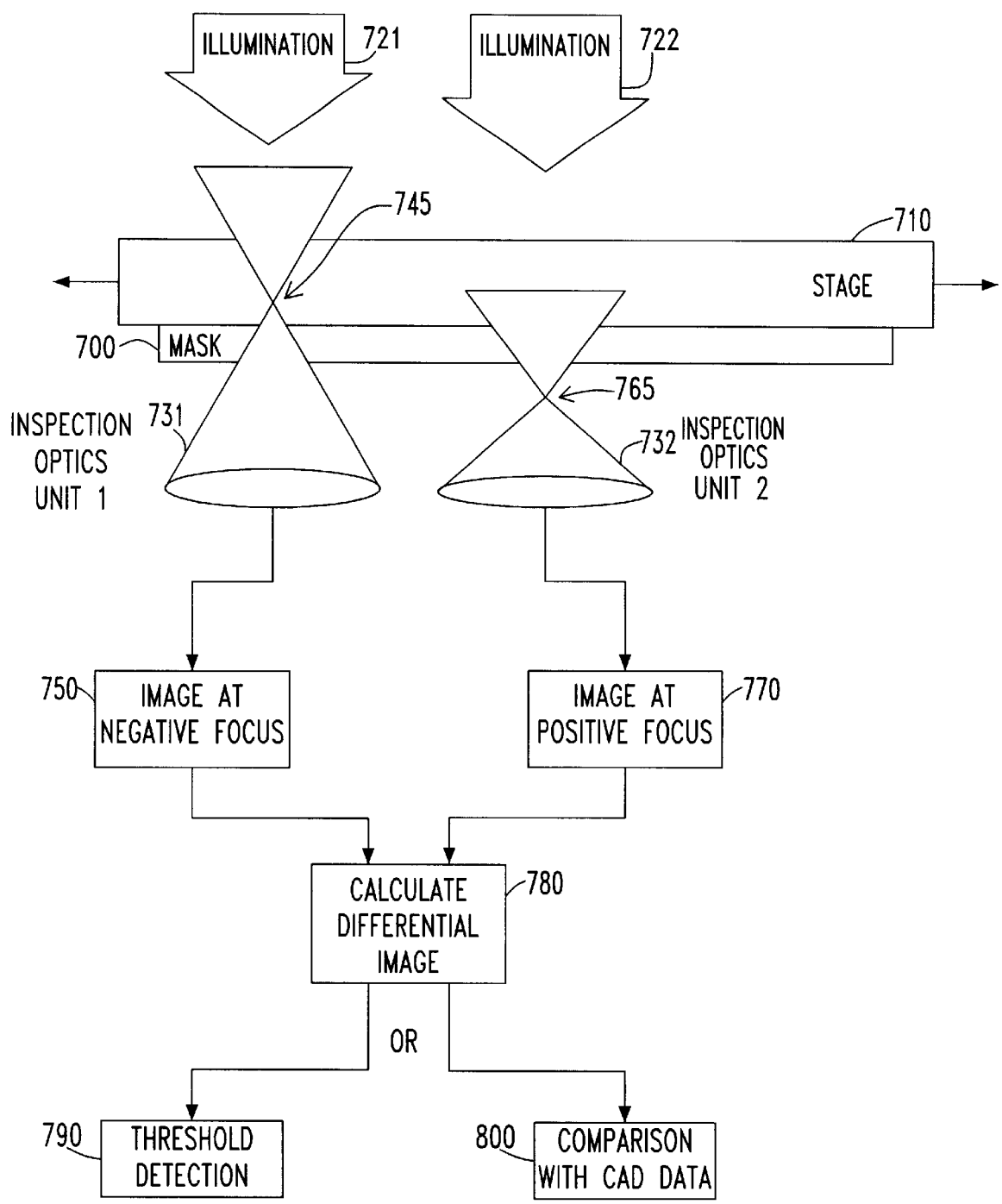
FIG. 11 shows a schematic diagram of an apparatus in accordance with a preferred embodiment of the invention, wherein the differential image of a mask located on a moveable stage is obtained in a single pass of the mask through parallel optical systems at a positive and a negative focus.

A schematic diagram of a new apparatus in accordance with a preferred embodiment of the invention is depicted in FIG. 11, wherein the inspection of the mask (700) located on the moveable stage (710) is achieved in a single pass of the mask. The system consists of two sets of inspection optics (731) and (732) of which one is focused in the negative direction relative to the mask (745) and the second is focused in the positive direction (765). As the stage is scanned, the image at the negative focus (750) and the image at the positive focus (770) are recorded and the differential image (780) is calculated by subtracting one from the other. In a similar fashion to the apparatus of FIG. 10, threshold detection (790) or a more sophisticated comparison with CAD data (800) can be used to identify the phase defects from the differential image.

Figure 7A:
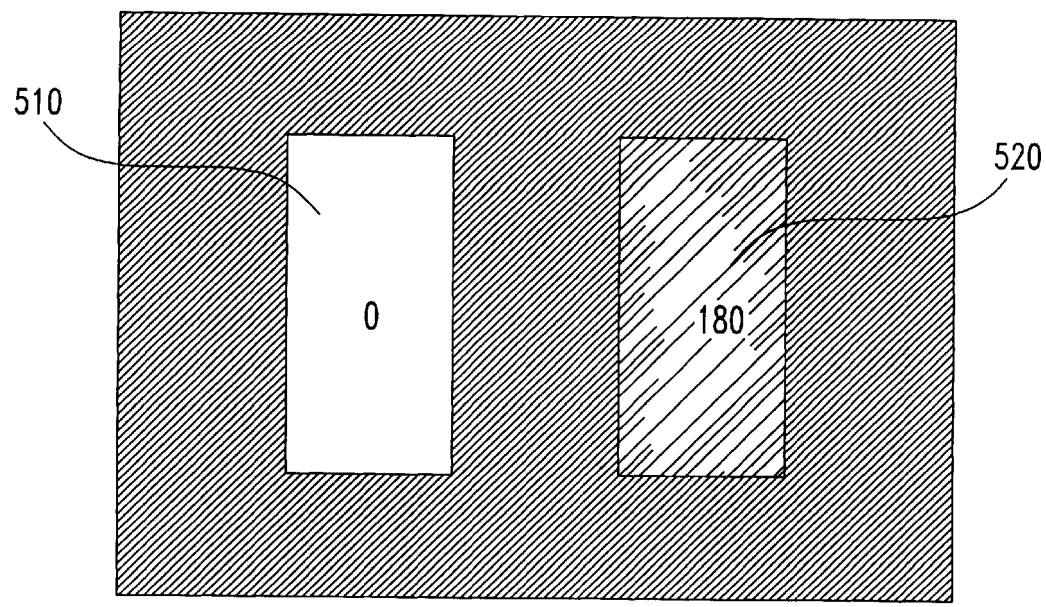
Figure 7B:
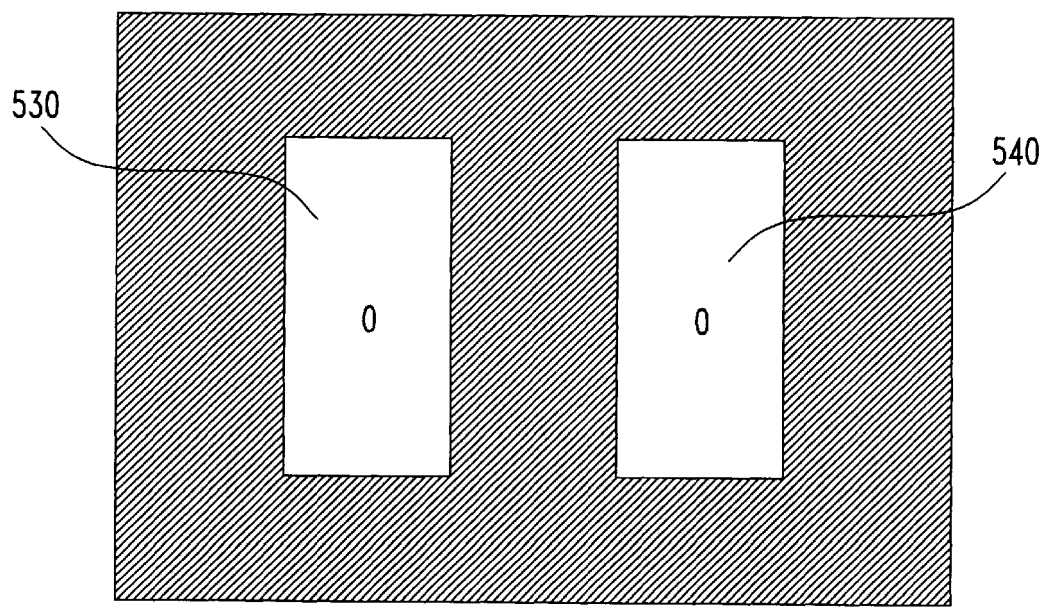
Figure 8A:
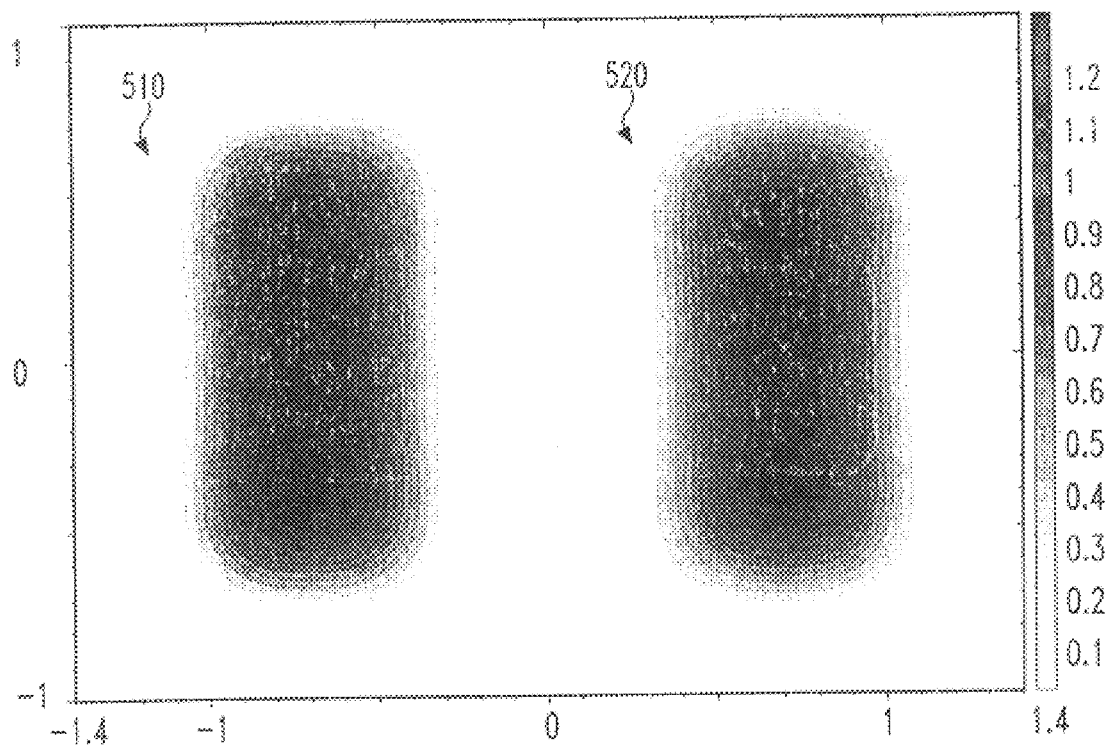
FIGS. 8a–8b are simulated images using standard industry practice for the properly fabricated shapes and for the missing shifter pattern depicted in FIGS. 7a–7b respectively, wherein small differences between the two images indicate that prior art inspection methods are insufficient to identify the absence of the phase-shifted pattern on a given shape.
Figure 8B:
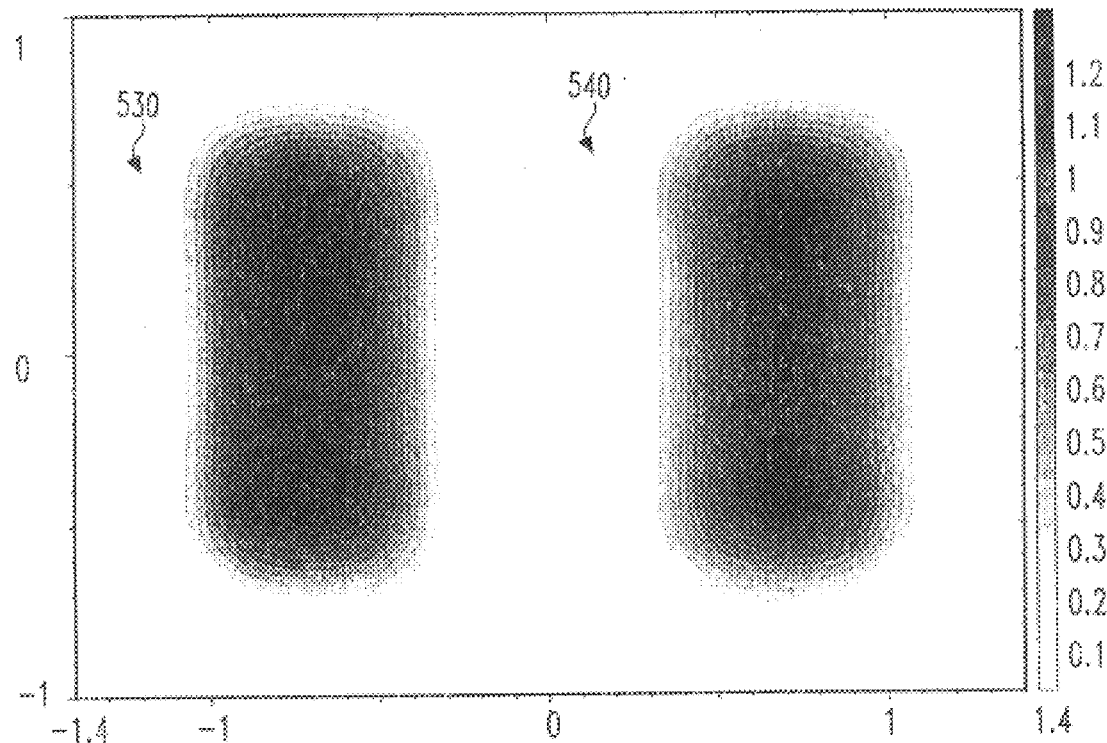
Figure 12A:
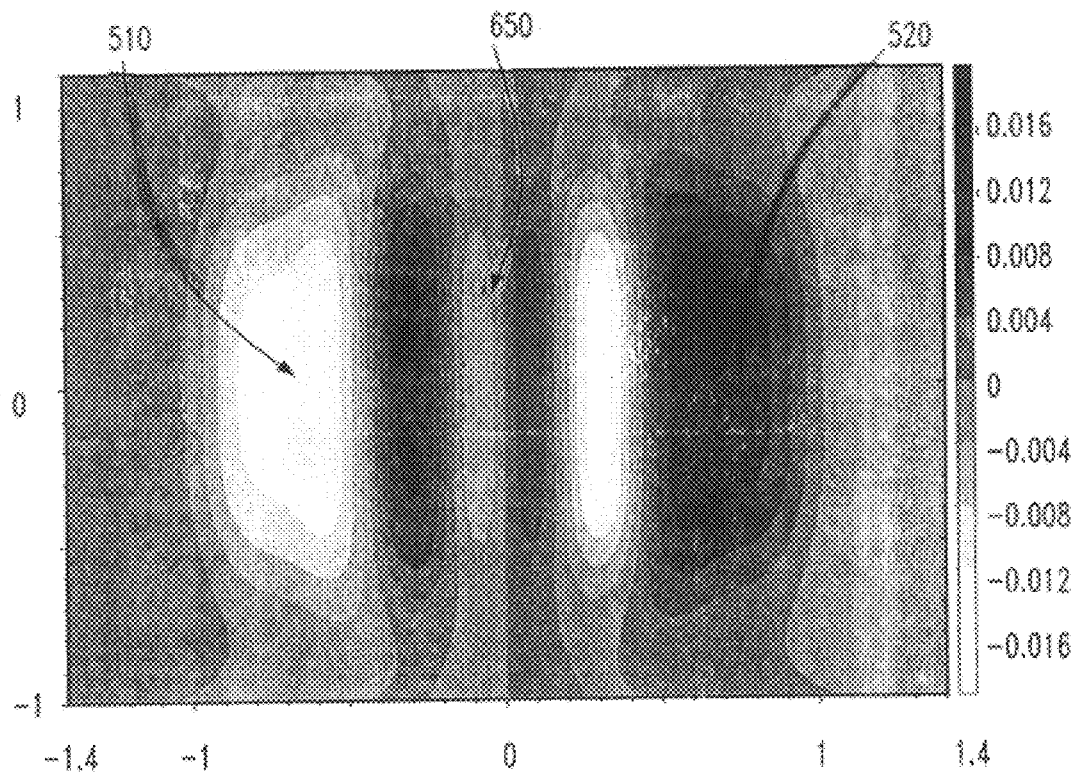
FIGS. 12a–12b show simulated differential images corresponding to FIGS. 7a–7b in accordance with a preferred embodiment of the invention, for detecting missing shifter patterns, wherein the zero-valued differential image of FIG. 12b is used to identify the missing shifter pattern of FIG. 7b.
Figure 12B:
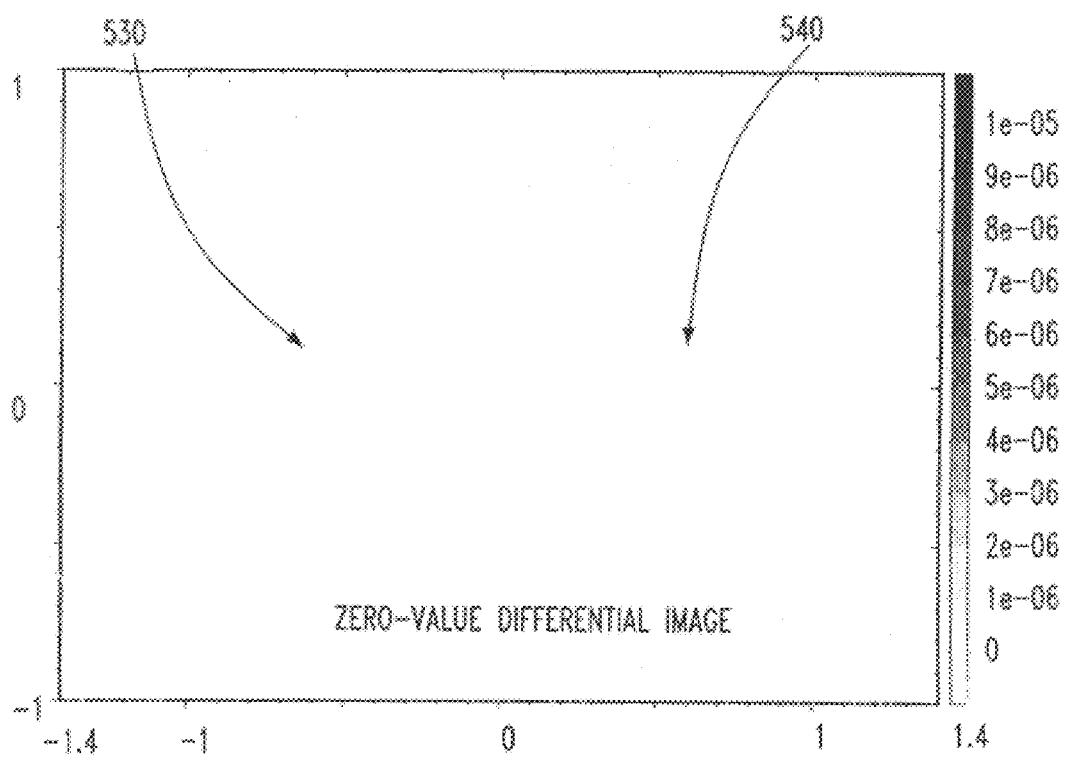

In another embodiment of this invention, the differential inspection method is used to detect the presence and/or the integrity of missing phase features on the mask, as shown in the previously described FIGS. 7a–7b. If the phase of the missing shifter is 180° relative to the stepper wavelength then this technique requires that the inspection be performed at non-actinic wavelengths (i.e., at a different wavelength than that used by the stepper). The results of the differential inspection method as previously described with ±1 Rayleigh unit of defocus are shown in FIGS. 12a and 12b for the patterns depicted in FIGS. 7a and 7b, respectively. When the mask has been fabricated properly as in the case for the differential image of FIG. 12a, the presence of the phase transition between shapes (510) and (520) is accentuated by rapid changes in the differential image at location (650). When the phase shifted pattern is missing as in FIG. 12b, no differential image is obtained, as shapes (530) and (540) behave symmetrically through focus. Once the differential image has been obtained from inspection such as in FIG. 12a or FIG. 12b, comparison of the differential image with the design data such as in FIG. 7a can be used to successfully identify any missing shifter patterns. This simplified threshold approach may suffice for verifying the presence of phase features on the mask but it may not be capable of confirming the integrity (i.e., shape and size) of the phase feature. Verification of phase feature integrity may require more sophisticated algorithms similar to proprietary algorithms used on existing optical inspection systems today to verify the integrity of non-phase features.

It should be clear to one skilled in the art that the embodiments described herein for detecting phase defects and missing shifter patterns can be combined to inspect for both conditions simultaneously using differential imaging at non-actinic wavelengths. In addition, the methods herein described are applicable to COG and alternating phase-shifting masks which provide a transmitting image during photolithographic patterning. It should be evident to those skilled in the art that these methods are equally applicable to other phase-shifting masks including attenuating PSM and rim PSMs. Furthermore, these methods are equally applicable to detecting phase defects and features when the photolithographic imaging is achieved using reflecting masks (e.g., extreme ultraviolet (EUV) lithography masks).

While this invention has been described with reference to a preferred embodiment thereof, it is to be understood that the method of the invention is not limited to the precise details and conditions disclosed and that various changes and modifications, may be made without departing from the spirit of the invention which is defined by the claims that follow.

What is claimed is:

1. A method for detecting phase features or phase defects on a photomask comprising the steps of:
   collecting images of said photomask at multiple focal planes of an optical inspection tool, said focal planes being positioned in a positive and a negative direction about an optimum focus of said optical inspection tool; and
   identifying elements of said images which behave asymmetrically relative to said optimum focus, said elements being categorized as said phase features or phase defects.

2. The method as recited in claim 1, wherein said photomask is inspected at a wavelength which said photomask is to be exposed during photolithographic patterning.

3. The method as recited in claim 1, wherein said photomask is illuminated by light at an inspection wavelength, and wherein a transmitted or a reflected image of said photomask is measured by an optical lens.

4. The method as recited in claim 3, wherein said transmitted or reflected image is measured by an objective at two focus points that are equally spaced about said optimum focus.

5. The method as recited in claim 1, wherein any said phase features characterized as being opaque or having a phase of 0° or 180° will produce identical images at positions symmetrically spaced about said optimum focus.

6. The method as recited in claim 1, wherein any said phase defects do not produce identical images at said positive and negative directions about said optimum focus.

7. The method as recited in claim 1, wherein said images are collected with an image size resolution defined by a wavelength ($\lambda$), numerical aperture (NA) and partial coherence ($\sigma$) of said optical inspection tool.

8. The method as recited in claim 7, wherein said images are collected on a high-NA optical inspection tool at a wavelength within an ultra-violet spectrum.

9. The method as recited in claim 7, wherein the distance from said optimum focus is selected to have a defocus step size of ±1 Rayleigh unit defined by:

$$\text{Rayleigh unit} = \lambda_i/(2*NA_i*NA_i),$$

wherein $\lambda_i$ and $NA_i$ are, respectively, said wavelength and said numerical aperture of said optical inspection tool.

10. The method as recited in claim 7, wherein the capability of detecting said phase features or phase defects of a desired size and phase are optimized by adjusting the distance from said optimum focus.

11. The method as recited in claim 1, wherein said images are collected concurrently or sequentially in any order.

12. The method as recited in claim 1, wherein said photomask is selected from the group that consists of a chrome-on-glass mask (COG), an alternating mask and an attenuated mask.

13. A method for detecting phase features or phase defects on a photomask comprising the steps of:
   collecting images of said photomask at multiple focal planes of an optical inspection tool, said focal planes being positioned in a positive and a negative direction about an optimum focus of said optical inspection tool;
   calculating a differential image of said mask by subtracting a first one of said images collected in one direction from a second one of said images collected at an opposite direction about said optimum focus; and
   identifying elements of said images having an absolute value larger than a fixed threshold which result in a non-zero value for said differential image, said non-zero value defining said phase features or phase defects.

14. The method as recited in claim 13, wherein said differential image is obtained during inspection as defocused images of said photomask are measured.

15. The method as recited in claim 13, wherein said differential image is obtained at two focus conditions after the entire photomask has been inspected.

16. The method as recited in claim 13, wherein said phase defects are located by searching for non-zero values in said differential image.

17. The method as recited in claim 13, wherein a minimum threshold value of said differential image is established to indicate the presence of said phase features or phase defects.

18. A method for detecting phase features or phase defects on a photomask comprising the steps of:
   collecting images of said photomask at multiple focal planes of an optical inspection tool, said focal planes being positioned in a positive and a negative direction about an optimum focus provided by said optical inspection tool;
   calculating a differential image of said mask by subtracting a first one of said images collected in one direction from a second one of said images collected at an opposite direction about said optimum focus;
   identifying elements of said differential image which result in a minimum threshold non-zero value for said differential image, said threshold defining said phase features or phase defects; and
   comparing the location of said elements at which said differential image exceeds said threshold to a predetermined data set representing desired phase features on said photomask, wherein an unmatched one of said locations is categorized as a phase defect.

19. The method as recited in claim 18, wherein all others of said phase features or phase defects of said differential image are reduced to a zero background intensity.

20. A method for detecting phase features or phase defects on a photomask comprising the steps of:
   collecting images of said photomask at multiple focal planes of an optical inspection tool, said focal planes being positioned in a positive and a negative direction about an optimum focus provided by said optical inspection tool;
   calculating a differential image of said mask by subtracting a first one of said images collected in one direction from a second one of said images collected at an opposite direction about said optimum focus; and
   comparing said differential image at two or more locations on said photomask at which a predetermined data set representing desired features on said photomask is identical, and wherein differences in said differential images at said locations are categorized as phase defects.

21. An apparatus for detecting phase features or phase defects on a photomask comprising:
   means for collecting images at said photomask at multiple focal planes of an optical inspection tool, said focal planes being positioned in a positive and a negative direction about an optimum focus of said optical inspection tool; and
   means for identifying elements of said images which behave asymmetrically relative to said optimum focus, said elements being categorized as said phase features or phase defects.

22. The apparatus as recited in claim 21, further comprising means for inspecting said photomask at a wavelength wherein said photomask is to be exposed during photolithographic patterning.

23. The apparatus as recited in claim 21, wherein said photomask is illuminated by light at an inspection wavelength, and wherein a transmitted or reflected image on said photomask is measured by an optical lens.

24. An apparatus for detecting phase features or phase defects on a photomask comprising:

means for collecting images of said photomask at multiple focal planes of an optical inspection tool, said focal planes being positioned in a positive and a negative direction about an optimum focus provided by said optical inspection tool;

means for calculating a differential image of said mask by subtracting a first one of said images collected in one direction from a second one of said images collected at an opposite direction about said optimum focus;

means for identifying elements of said differential image which result in a non-zero value for said differential image, said non-zero value defining said phase features or phase defects; and means for comparing the location of said element at which said differential image exceeds a threshold of a predetermined data set representing desired phase features on said photomask, wherein an unmatched one of said locations is categorized as a phase defect.

\* \* \* \* \*